United States Patent [19]

Kim

[11] Patent Number: 4,986,658
[45] Date of Patent: Jan. 22, 1991

[54] TRANSIENT SPECTROSCOPIC METHOD AND APPARATUS FOR IN-PROCESS ANALYSIS OF MOLTEN METAL

[75] Inventor: Yong W. Kim, Bethlehem, Pa.
[73] Assignee: Lehigh University, Bethlehem, Pa.
[21] Appl. No.: 341,748
[22] Filed: Apr. 21, 1989
[51] Int. Cl.$^5$ .......................... G01J 3/443; G01J 3/18; G01N 21/63
[52] U.S. Cl. ..................... 356/318; 356/328; 356/334
[58] Field of Search ......................... 356/313, 317, 318

[56] References Cited

U.S. PATENT DOCUMENTS

| | | | |
|---|---|---|---|
| 3,645,628 | 2/1972 | Bojic et al. | 356/313 |
| 4,182,574 | 1/1980 | Quillfeldt | 356/318 |
| 4,652,128 | 3/1987 | Tsunoyama et al. | 356/318 |

*Primary Examiner*—Vincent P. McGraw
*Attorney, Agent, or Firm*—Oblon, Spivak, McClelland, Maier & Neustadt

[57] ABSTRACT

A method and apparatus for in-process transient spectroscopic analysis of a molten metal, wherein a probe containing a pulsed high-power laser producing a pulsed laser beam having a substantially triangular pulse waveshape is immersed in the molten metal and irradiates a representative quantity of the molten metal. The pulsed laser beam vaporizes a portion of the molten metal to produce a plasma plume having an elemental composition representative of the elemental composition of the molten metal. Before the plasma plume reaches thermal equilibrium shortly after termination of the laser pulse, a spectroscopic detector in the probe detects spectral line reversals, as caused by absorption of radiation emitted by the hotter inner portion of the plasma plume to relatively coller outer portions of the plasma plume, during a short first time window. Thereafter, when the afterglow plasma is in thermal equilibrium, a second spectroscopic detector also in the probe performs a second short time duration spectroscopic measurement. A rangefinder measures and controls the distance between the molten metal surface and the pulsed laser.

52 Claims, 6 Drawing Sheets

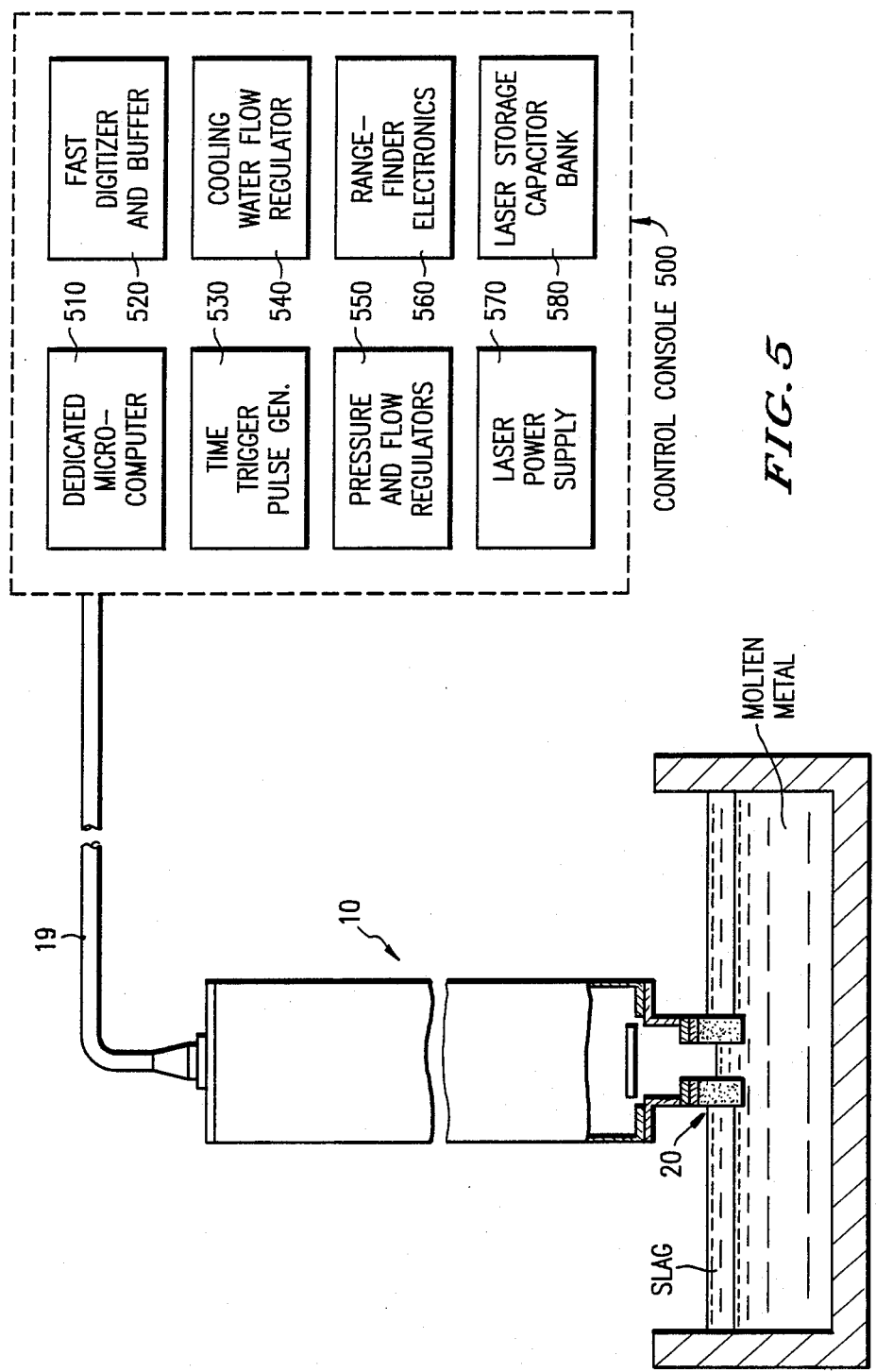

TRANSIENT SPECTROSCOPIC METHOD AND APPARATUS FOR IN-PROCESS ANALYSIS OF MOLTEN METAL

BACKGROUND OF THE INVENTION

1. Field of the Invention

This invention relates to a transient spectroscopic method and apparatus for in-process analysis of molten metal to determine the elemental composition of the molten metal.

2. Discussion of Background

Determination of the elemental composition of molten metals as one of the process control data requires that the measurement be of real-time, in situ nature. The successful technique must be able to overcome most variations that exist of the thermal and fluid dynamic state of the molten metal and of the chemical properties of the slag layer above. Furthermore, the technique cannot rely on any physical phenomena which depend sensitively on the physical properties of the molten metal such as shear viscosity, surface tension, elemental vapor pressure and sound speeds. Of course, any sensor elements employed in the technique must either be able to survive the bath temperature or be provided with cooling without risking freeze-up of the slag or molten metal on them.

These requirements eliminate virtually all but the two following approaches: (a) excitation and subsequent spectroscopic examination of the particulate and gaseous effluents from the molten metal bath and (b) rapid vaporization and atomic excitation of a vapor plume from a slag-free molten metal surface by intense laser pulses, followed by spectroscopic analysis of the emission spectra. The first approach is advantageous in that measurement activities may be taken outside of a given furnace, thus allowing for extensive instrumentation, and is intrinsically well suited for generating a great deal of process data. It is, however, burdened with the need to determine under real-time conditions the extent of elemental contributions to the effluents by the slag in relationship to the molten metal. Prior investigation into the mechanisms of particulate production in steel furnaces has shown that the relative contributions depend strongly on the intensity of gas bubbling in the molten metal bath and the furnace temperature profile as well as the slag composition and the nature of nucleation centers for particulates (see T. W. Harding et al., "Direct Sampling of Gas and Particulates from Electric Arc Furnaces", in *Proceedings of APS/AISI Conference on Physics in Steel Industry, Lehigh University*, 1981. American Institute of Physics Conference Proceedings No. 84 (1982), pp. 362-376, and J. R. Porter et al., "Characterization of Directly Sampled Electric Arc Furnace Dust", *Proceedings of APS/AISI Conference on Physics in Steel Industry, Lehigh University*, 1981, American Institute of Physics Conference Proceedings No. 84 (1982), pp. 337-393.). While there are ways to meet this need, it is clear that extensive research must be carried out.

Examples of the first approach above outlined are discussed in U.S. Pat. No. 4,730,925 to *Chiba et al* and *Frazer*, "Continuous Monitoring of Melt Composition", NASA Tech Brief, Vol. 8, No. 2, Item No. 34, 1983.

Various attempts reported in the patent literature have been made to implement the second approach above noted. In U.S. Pat. No. 4,578,022 to *Kenney*, there is disclosed an apparatus for generating an aerosol powder from a metal melt. According to *Kenney*, a probe having an atomization dye is partially immersed in the metal melt so that the melt passes through an orifice in the atomization dye to create an aerosol powder. The aerosol powder is then transported by an inert gas to an inductively coupled plasma torch remote from the probe where the metal powders are heated and excited to emit atomic spectra characteristic of their constituent elements. However, the production of the aerosol powders skews the compositional distribution of the elements within each aerosol powder particle because the high evaporation elements are driven out by evaporation if the carrier gas is still hot. Further, all the aerosol particles are not the same size, with a result that the smaller the size of each aerosol particle, the larger the surface area to volume ratio of that particle. Therefore, the particles actually analyzed typically are those aerosol particles which exhibit the effect of more evaporation because many of the larger particles are lost by sedimentation, i.e., sticking to the walls during transport. Thus, the chemical composition of the molten metal is not accurately represented by the chemical composition of the aerosol powders subjected to analysis. Further, transportation of the aerosol powders to remote processing increases the likelihood of contamination of the aerosol powder. Subjection to a remote plasma flame can potentially compound the problem of contamination, so that the spectroscopic measurement subsequently performed are inherently inaccurate.

U.S. Pat. No. 4,598,577 to *Jowit* teaches laser ablation and evaporation of a molten metal by means of a laser housed in a probe which is immersed into the molten metal. Accordingly to *Jowit*, all or part of the vaporized metal is transported to a remote analytic apparatus including a plasma torch for heating the vaporized metal and a spectrograph for spectroscopic analysis of the plasma produced by the plasma torch. However, transporting of vaporized metal which is recondensed into particulates suffer from the same loss of larger particulates and preferential evaporation, which skews the subsequent spectroscopic analysis.

In British Patent No. 2,154,315A to *Spenceley et al*, on the other hand, a portion of a metal melt is excited by means of a pulsed laser beam and the radiation transmitted from the excited metal melt is transmitted through a light guide to an off line spectrometer for spectroscopic analysis of the spectrum produced by the excited portion of the melt. This technique, however, suffers due to the fact that a considerable amount of radiation from the excited melt does not enter the light pipe, and there is considerable absorption of this radiation during transmission via the light pipe to the analysis equipment. Further, this absorption of the radiation by the light pipe varies as a function of frequency, and thus impedes accurate measurement of the relative amplitudes of the various spectral components, and indeed prevents on occasion the actual detection of the severely absorbed spectral components.

SUMMARY OF THE INVENTION

Accordingly, one object of this invention is to provide a new and improved method and apparatus for inprocess transient spectroscopic analysis of molten metal, which are free of the problems of the prior art and which provide an accurate and reproducible indication of the composition of the molten metal under evaluation.

Another object of this invention is to provide a novel method and apparatus, as above noted, whereby it is possible to monitor, in real time, the elemental composition of a molten metal in a furnace producing a metal of desired composition, as in steelmaking and subsequent alloying operations, thereby to guarantee the chemistry, subsequent properties, and performance of the product.

A further object of this invention is to provide a novel method and apparatus, as above noted, by which measurements can be rapidly obtained.

These and other objects are achieved according to the invention by providing a new and improved method and apparatus for in-process transient spectroscopic analysis of a molten metal, wherein a probe containing a pulsed high-power laser producing a pulsed laser beam having a substantially triangular pulse waveshape to irradiate a representative quantity of the molten metal is immersed in the molten metal. The laser is energized and vaporizes a portion of the molten metal to produce a plasma plume having an elemental composition representative of the elemental composition of the molten metal. According to the invention, shortly after termination of the laser pulse, e.g., within 50-200 nsec of the laser outputting peak power, spectral line reversals in the spectrum of the plasma plume, as caused by absorption of radiation emitted by the hotter inner portion of the plasma plume to relatively cooler outer portions of the plasma plume, are spectroscopically detected during a short first time window by means of a first spectroscopic detector also located in the probe. Thereafter, when the afterglow plasma is in thermal equilibrium, a second short time duration spectroscopic measurement is taken by means of a second spectroscopic detector also located in the probe.

According to the invention, at least one rangefinder is employed to measure and to control the distance between the molten metal surface and the pulsed laser. Further, in recognition of the spatial dependence of the temperature, vapor-phase elemental number density and degrees of ionization of each species within the plasma plume as a function of a position in reference to the molten metal surface and the laser beam axis, the spectroscopic measurement for detecting spectral line inversion is performed a predetermined distance away from the surface of the molten metal and a predetermined distance from the laser beam axis.

Within the probe of the invention, there is provided a pair of spectrographs each having a diffraction grating or the like coupled to a gated, intensified photodiode array detector. Each spectrograph is used to perform a spectral analysis during a respective of the line above-noted. In order to improve resolution and yet promote miniaturization, each spectrograph employs between the diffraction grating and the detector folded optics which produces multiple reflections of the separated spectral components, thereby increasing the total distance travelled by the various spectral components to increase the spatial separation therebetween. Since not all spectral regions are of interest, selectively controlled segmented mirrors are used to select only those spectral regions of interest and reflect only such spectral regions to the detector array.

Once the emission spectrum is detected, the present invention employs iterative processing techniques to perform spectral pattern recognition. The envelope of the detected spectral components is differentiated to determine peaks, and to each detected peak is fitted a predetermined function, such as a Gaussian function or a Lorentzian function, or a hybrid thereof having an amplitude dependent on the amplitude of the detected peak, and a predetermined width. Then a synthesized spectrum is formed by summing the individual functions fitted at each detected peak, and the synthesized spectrum is compared with the actually detected spectrum to produce an error signal. The error signal is then used to change at least one parameter, e.g. amplitude and/or width of the fitting functions. A new synthesized spectrum is formed, and again compared with the actually detected spectrum to produce a new error signal. The processing continues until the error signal is decreased to a predetermined limit, at which point the amplitudes and separations of the peaks of the synthesized spectrum well define the elemental composition of the molten metal.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 5 is a schematic illustration illustrating the probe of the invention in relation to the molten metal and a control console during operation of the apparatus of the invention.

DESCRIPTION OF THE PREFERRED EMBODIMENTS

The present invention is directed to a spectroscopic method and apparatus for in-process analysis of molten metal generally employing the second approach discussed in the background of the invention, i.e., the rapid vaporization and atomic excitation of a slag-free molten metal surface by intense laser pulses, followed by spectroscopic analysis of the emission spectra.

Figure 1:
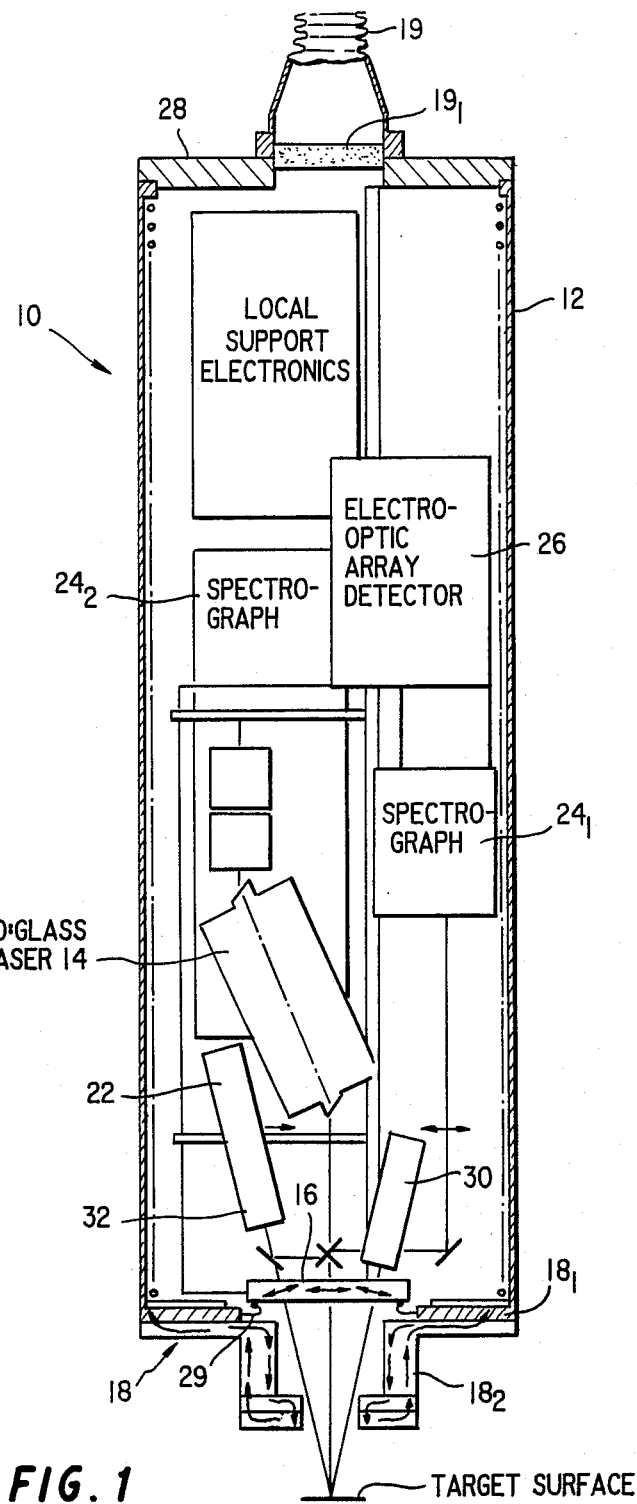
FIG. 1 is a schematic illustration illustrating the structural components of the probe of the invention.

Referring now to the drawings, wherein like reference numerals designate identical or corresponding parts throughout the several views, and more particularly to FIG. 1 thereof, the present invention includes a probe 10 which penetrates the slag layer. The probe 10 is thermally protected by means of a vacuum tight protective shell 12 and includes a high-power pulsed laser 14, for irradiating a target area on the surface of the molten metal with a focused pulsed high power laser beam, as discussed in more detail hereinafter. The laser beam is focused by an optics block 16 into a spot of sufficient size to heat and plasmatize a representative quantity of the molten metal. Spectral analysis is then performed in situ on the radiation emitted by the plasma plume produced by the laser beam, as discussed hereinafter.

The protective shell 12 basically includes a precision-machined, stainless steel vessel of tubular construction including inner and outer tubings. The outer tubings are assembled together in such a way that cooling water at high pressure (150 psi) flows down the full length of the probe 10 and the front face at the leading end 18 of the probe 10 as shown schematically by the arrows 10, and returns to be discharged. The innermost tubing allows a flow of cooled inert gas, e.g., argon, through the center to cool the optical components, including the laser 14, and to prevent metallic vapors and particulates from reaching the optics block through the open, leading end 18 of the probe.

As shown in FIG. 5, the leading end 18 of the probe is fitted with a snap-on ablative or non-wetting refractory sheath 20. The sheath 20 penetrates the slag layer and exposes the molten metal surface to the laser 14 and spectroscopic detection optics, all housed in the probe. The role of the sheath 20 is to keep the cooled stainless steel surfaces from coming into contact with either the slag or molten steel so as to prevent their freeze-up on the probe. Such a sheath layer permits multiple immersions of the probe into the melt without its replacement.

The leading edge 18 is provided with three separate coaxial grooves machined in an upper bottom flange $18_1$. The innermost groove communicates with tubing lining the probe 10 and provides a path for pneumatic control of the molten metal level at the open end 18. The outer coaxial grooves communicate with the outer tubings lining the probe 10 and provide the flow path in the leading end 18 for the flow of water coolant, shown by the arrows $18_2$.

The design of the probe 10 of the invention permits rapid approach to, and withdrawal from, the molten metal surface, which is representative of the bulk composition, by the probe. This operation is effected by an electromechanical manipulator (not shown) to which the probe is attached. The refractory sheath 20 of the probe's leading end 18 is the only component which is exposed to and/or comes into contact with the molten metal at temperatures up to 1600° C. or higher. The probe may be driven toward the surface or away from it in any manner at speeds as high as $10^3$ cm/sec. The probe design permits penetration of slag layers by the sheath 20 to reach a representative molten metal surface. The leading end 18 is a tubular extension of the probe and is protected by the non-wetting refractory sheath 20 and provided with the cooling inert gas flow through two tubular layers of coaxial design similar to the water cooling arrangement described above. By real-time control of the gas flow rate and pressure, the sheath 20 is rendered to have a solid-like property during the penetration through the slag and, once in the molten metal pool, becomes a hollow tube into which the metal is drawn to a predetermined level suitable for laser excitation.

Survivability of the probe head is assured by a combination of active cooling by water and gas flows, thermal shielding by layers of metal and refractory sheath and a short period of exposure limited to usually less than a minute. The coolant water and gas flows are supplied to the probe 10 via umbilical cord 19 which also provides power and signal lines to the interior of the probe via a vacuum feedthrough block 21. The refractory lining is of non-wetting type in the sense that the sheath 20 remains free of build-up by solidified slag or metal for repetitive penetrations. It takes the form of non-wetting solid refractories, such as Masrock or ablative refractories consisting of alternating thin layers or two different melting points materials or a combination of the two.

The probe 10 contains in addition to the laser 14, a rangefinder 22, spectrographs $24_1$, and $24_2$ with photodetectors equipped with gated intensifiers and other associated optics (not shown). The collimated beam of the laser 14 is focused onto the molten metal surface by a lens of the optics block 16 at a preset distance away from this lens. Energization of the laser 14 is controlled by the rangefinder 22 so that the laser irradiates the molten metal when the rangefinder 22 determines that the surface of the molten metal is at the predetermined distance from the lens of the optics block 16. Optical emissions from the molten metal irradiated by the laser 14 are detected at predetermined time intervals by spectrographs $24_1$, $24_2$, and associated electroptic array detectors of which only the detector 26, is shown in FIG. 1. The optics block 16, rangefinder 22, spectrographs $24_1$, $24_2$, and electrooptic detectors 26, as well as local support electronics 27 therefore are mounted on an assembly rigidly supported by an upper flange 28, of the probe 10. In order to couple the optics block 16 to the upper bottom flange $18_1$ of the probe, there is provided a bellows 29 interconnecting the optics block 16 to the flange $18_1$. The bellows 29 is flexible in order to accommodate thermally induced dimensional variations. Bellows 29 maintains the vacuum seal of the interior of the probe 10 without impinging on the integrity of the optical alignment from the laser 14 to the spectrographs $24_1$, $24_2$.

Next described are design considerations regarding the laser 14 of the present invention. Several considerations govern the design and choice of a particular laser by which to implement the laser 14. First, the laser 14 must produce at the surface of the molten metal a pulsed laser beam of sufficient intensity over a sufficiently large area to produce a plasma plume which has a composition representative of the composition of the molten metal. To that end, the size of the focal spot of the pulsed laser beam on the molten metal must be large enough to cover a representative sample of the molten metal to assure that local microscopic inhomogeneities in the molten metal do not affect subsequent spectroscopic measurements. Once again, the objective is to produce a plasma plume having the same elemental composition of the molten metal. This is accomplished by an extremely rapid rate of energy delivery, possible with a Q-switched laser, to the target region, far greater than the rates of heat transfer and elemental diffusion in the molten metal. In this respect, it is necessary that the thermal diffusion front produced by heating of the metal by the pulse laser beam proceeds at the same rate of the evaporation front caused by evaporation of the molten metal to assure that differences in evaporation rates of different constituent elements do not effect the elemental composition of the plasma plume. The net result is rapid and complete vaporization of all constituent elements of the target region, regardless of the elemental dependence of the equilibrium rate of evaporation. The vapor plume is further heated by the inverse Bremsstrahlung and multiphoton processes and becomes a plasma of high temperature and significant ionization. The elemental composition of the molten metal can then be determined by a time-resolved spectroscopic measurement of the emission spectrum of the plasma plume.

A further consideration in the design of the laser 14 is the waveform of the laser pulse emitted by laser 14. It has been determined according to the invention that the laser pulse from the laser port 14 should have a substantially triangular (with acute angles) shape, should be of intense power, and should be of short time duration. The triangular wave shape is dictated by the fact that if the rise time of the laser pulse is too fast, as occurs with a rectangular or a right angle triangular wave shape, the plasma would be element poor. This results when the relatively quick heating produced by the rapid rise time of the rectangular laser pulse would not permit sufficient heating of a sufficient quantity of the molten metal before evaporation of the molten metal begins. With the rectangular (i.e., rapid rise time) pulse, initially ionized vapor would reflect further laser light and prevent such laser light from reaching the target before sufficient heating of the molten metal is achieved. As a result, as above noted, if a rise time is too fast as occurs with the rectangular pulse, the plasma would be element poor.

On the other hand, if the rise time of the pulsed beam from the laser 14 is too slow, then heating of the molten metal results in the evaporation front not matching the thermal diffusion front, resulting in the elemental composition of the plasma plume not being representative of the molten metal. Thus, it has been determined that a substantially triangular pulse width having a time duration of 50–100 nsec at the halfwidth, a rise time of 50 ± 20 nsec, and a decay time of 150 ± 50 nsec as produced by a Q-switch Nd:glass, ruby or $CO_2$ laser meets the heating requirements of the present invention. In view of the portability requirement of the entire sensor-probe, it is advantageous to employ the Nd:glass laser, with the laser having a sufficiently high power density ($>10^9$ W/cm$^2$).

To assure that the plasma plume has a composition representative of that of the molten metal, the Q-switched laser of the present invention produces at the surface of the molten metal a focus spot having an area of 1–4 mm$^2$, typically 2 mm$^2$, at the stated power density of $>10^9$ W/cm$^2$. This can be achieved by means of a Q-switched laser which operates in multimode operation, for example as achieved by using a larger rod and shorter cavity length to support many oscillation modes within the laser by supporting a recirculating wave over many different routes. Typically, the required focal spot size can be achieved by a laser supporting more than four fundamental modes, typically around a dozen fundamental modes.

By selection of the laser operation as above described, the present invention enjoys reproducible production of a plasma plume which is representative of a molten metal in its elemental composition. This is achieved by the exacting combination of three key elements: wide area focusing through multimode operation of the laser, above-threshold operation in power density of the laser, and control of the temporal profile of the laser pulse. As above discussed, the laser pulse must couple to a significant quantity of the molten metal in order to avoid adverse effects of microscopic inhomogeneities in the melt, and to evaporate, heat and ionize the sample to a robust plasma plume in a manner which does not alter the elemental composition from that of the melt by element-selective evaporation. This requirement is quantified in terms of the evaporation front moving as fast as the thermal diffusion front travelling into the bulk of the molten metal (see Y. W. Kim, "Fundamentals of Analysis of Solids by Laser Produced Plasmas," in *Application of Laser Plasmas*, eds. R. J. Radziemski and D. A. Cremers, Marcell Dekker (in press)). As above noted, these critical requirements are met simultaneously by focusing the laser beam onto an area on the order of 1–4 mm$^2$, considerably larger than a diffraction limited focal spot of a TEM$_{oo}$ mode laser output, at a power density on the order of 10$^9$ W/cm$^2$ during a triangular pulse duration on the order of 70 nsec at the pulse halfwidth.

Thus, the present invention employs extremely tightly controlled operation of the laser for high pulse-to-pulse reproducibility. The laser 14 has been designed for extreme stability of the laser cavity against thermal and mechanical variability. Active temperature control of the laser cavity as described above is employed in order to minimize the environmental variations, using an over-sized oscillator of a Nd:glass medium, giving a large pulse output at 1.06 $\mu$m in wavelength. Other laser media and wavelengths can be employed.

At the sufficiently high power density produced by the above noted laser, the plasma plume thereby produced attains a maximum temperature and electron density within the life time of the 50–200 nsec laser pulse and exhibits a spectrum characterized by a broad continuum with self-reversed resonance lines of the constituent atomic species of the plume. These line reversal results from the fact that the plasma plume has a steep temperature gradient about the core where the strong continuum originates by the Bremsstrahlung and Stark broadening processes. Therefore, the continuum radiation from the hotter central portion of the plasma plume becomes absorbed while going through the relatively cooler outer region of the plume, by the cooler atomic elements which are primarily populating their respective ground states. The result is a diminution of the continuum intensity at wavelengths corresponding to the resonance lines of all elements by various amounts determined by the absorption line profiles of individual resonance lines. According to the present invention it is recognized that this spectrum of line reversals occurring shortly after the creation of the plasma plume is of great value in simultaneous multi-element analysis because a) the spectrum is simple, containing primarily the self-reversed resonance lines; b) all of the necessary lines for detection of the elements of interest (P, S, Sn, B, Si, Mg, Pb, C, Zn, Cu, Co, Ni, Fe, Al, Mn, Ca, Cr, V, Ti, Na) are contained in the uv-visible range of 1750–7000 Å; and c) it is sensitive to small concentrations. Thus, according to the present invention, an approximately 20 nsec portion of this line reversal spectrum is spectroscopically analyzed by means of one of the spectrographs 24$_1$, 24$_2$ for full determination of the elemental composition. The spectroscopic analysis of the line reversal spectrum occurs according to the present invention approximately 50–200 nsec and less than 500 nsec after the laser 14 reaches peak power (i.e., before the plasma reaches thermal equilibrium).

As recognized according to the present invention, a second opportunity for elemental spectral analysis comes shortly after the conclusion of laser heating, when the plasma plume enters the afterglow decay mode. The afterglow may last as long as 500 nsec to 20 $\mu$sec, depending upon whether the ambient is a vacuum or a gaseous medium at high pressure. The line reversal phenomenon investigated during the first time window for spectral analysis ceases as the plasma temperature and its gradient erode due to radiative cooling and particle transport processes and the plasma becomes optically thin. Thereafter, when the plasma plume is in thermal equilibrium, that is when the time between collisions between atoms and ions in the plasma plume is short in comparison to the time during which the average size of the plasma is changing or cooling by radiation, according to the invention there is performed a second time-resolved spectroscopic measurement on the radiation emitted from the plasma plume. At that time, all emission lines become narrow and better defined although spectral resolution becomes more involved due to the appearance of the resonance as well as non-resonance lines. In this second measurement, the time window for measurement of a molten metal in a vacuum furnace may be 20 to 500 nsec long, beginning at somewhere about 250 nsec after the Q-switching of the laser.

Thus, according to the present invention, for each plasma plume produced by excitation by a singular triangular laser pulse above discussed, two different time windows for spectroscopic analyses of the plasma plume are established. In the first time window, the line reversal spectrum shortly after the termination of the laser pulse is spectroscopically analyzed, while in the second time window the emission line spectrum during the afterglow period is analyzed. Timing of the emission line spectrum during the afterglow period depends on the ambient gas pressure. In vacuum furnaces, the optimal time for the second window is for several hundred nsec starting about 250 nsec after the start of the laser pulse. In furnaces operating at atmospheric pressure, the time duration of the second window during which spectroscopic analysis is performed is about 500 nsec starting at 1 to 5 $\mu$sec after the initiation of the laser pulse. The time duration of the measurement windows is determined by the radiation fluxes and associated photon statistics which affect the signal to noise ratio of the detected spectral intensities. The optimum duration varies somewhat depending on the laser parameters. Regardless of whether operation is at a vacuum or under atmospheric pressure, in either case the determining factor in taking the spectroscopic measurement during the afterglow period is that the condition of local thermodynamic equilibrium has been achieved in the afterglow plasma. The present invention therefore precisely times the application of laser energy and the setting of the gating periods for spectroscopic analyses in the two time windows, which are critical to reproducibility of the spectral data.

As above noted, for each laser pulse, two time-resolved spectroscopic measurements are performed, by means of a pair of spectrographs $24_1$ and $24_2$, each having associated dispersive instruments, such as a spectrograph containing an Echelle grating, for producing high dispersion but compact display of the spectrum, and respective photoelectric detectors equipped with gated channel plate intensifiers. The spectrographs are of miniaturized design of sufficient dispersion for placement within the probe. The detector assemblies are likewise mounted in the probe. Provisions for shielding against electromagnetic interference are made to maintain the integrity of the electronics associated with the spectrographs in the presence of the high voltage switching activities required for the operation of the laser 14. The absolute fix on elemental concentrations by wt.% is made by a calibration of the spectra with either molten metal samples or solid metal samples of known composition. Either of the line reversal spectrum and the line emission spectrum is sufficient for composition analysis. Use of the two spectra derived during the two time windows not only provides two independent opportunities for analysis but also complements each other and helps remove whatever ambiguities that may be found in one or the other.

Figure 3A:
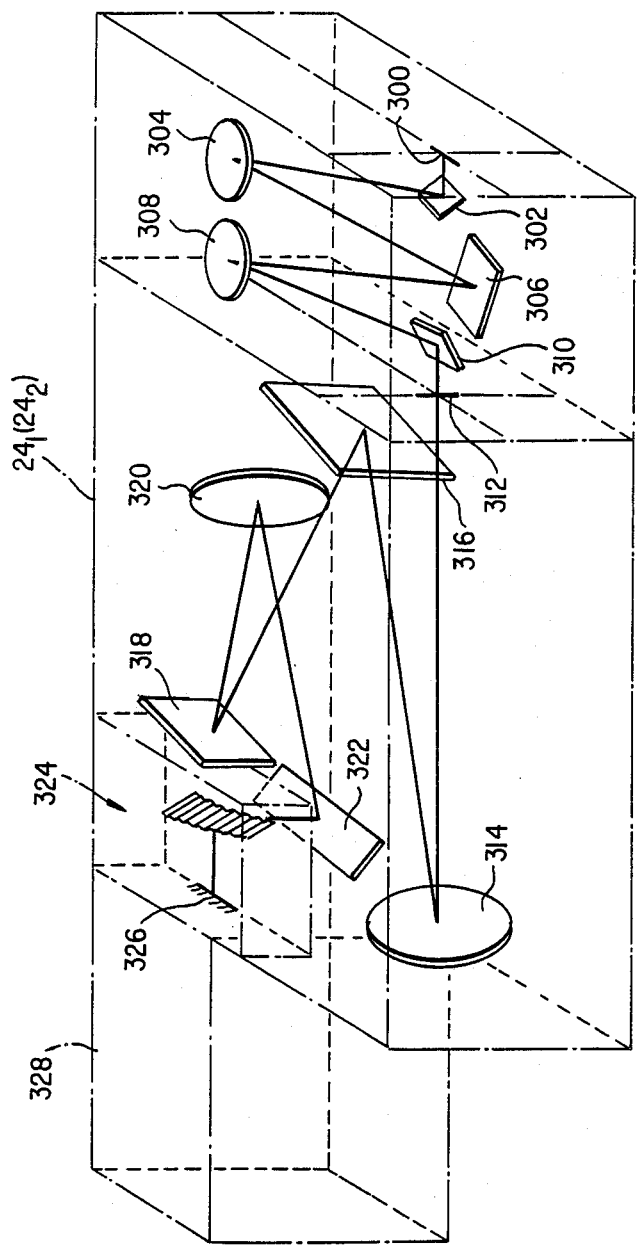
FIGS. 3a and 3b are schematic illustrations of the spectrograph optics of the spectrographs of the present invention.
Figure 3B:
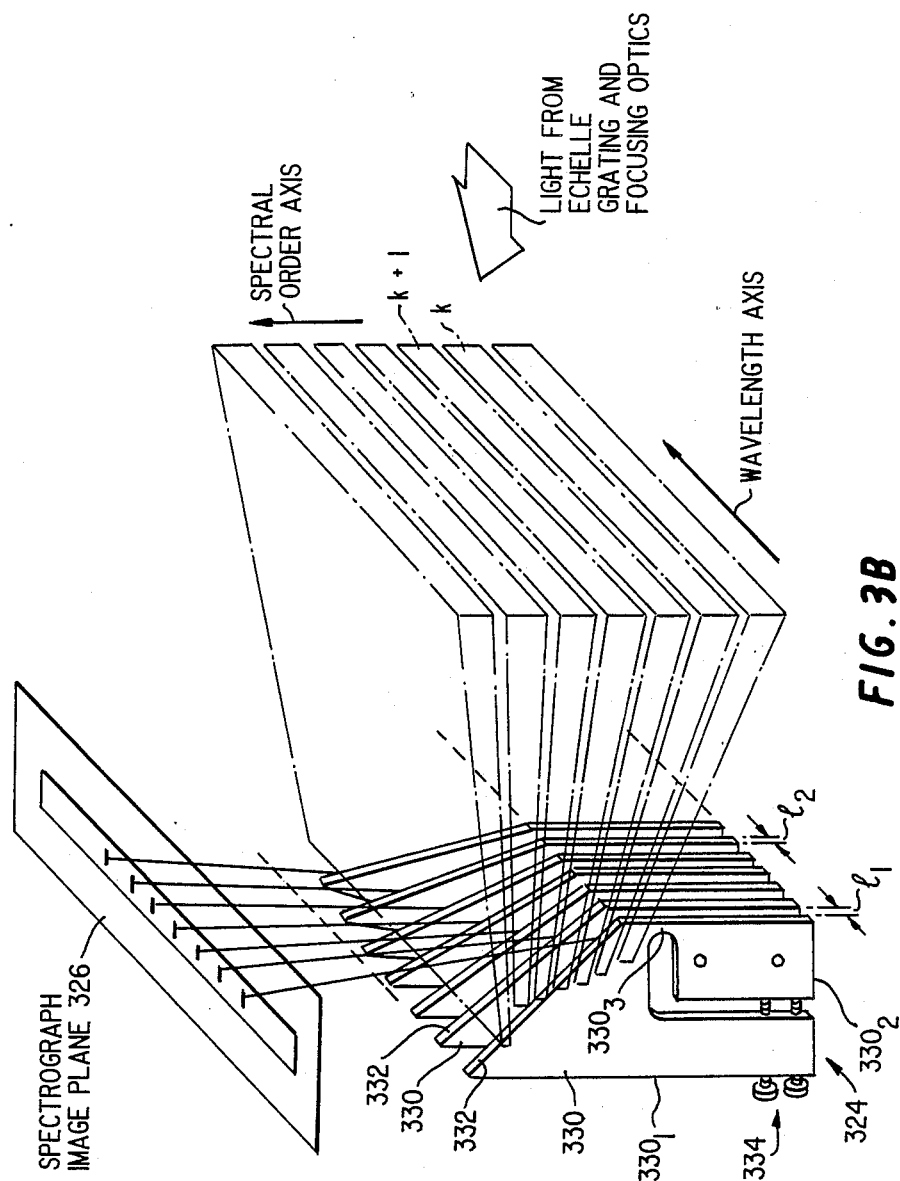

FIGS. 3a and 3b schematically illustrate the design of the spectrographs $24_1$ and $24_2$, which are identical, as well as a respective photoelectric detector 26 optically coupled thereto. As shown in FIG. 3a, the input to the spectrograph is a horizontal slit 300. Light passing through the slit 300 is reflected via plane mirror 302 and spherical mirror 304 to diffraction grating 306. Diffraction grating 306 passes the light via a spherical mirror 308 and plane mirror 310 to a vertical slit 312. Light passing through the vertical slit 312 is applied to a spherical mirror 314 and then to an Echelle grating 316 which produces high dispersion, and from there via folded optics formed by plane mirror 318, spherical mirror 320, and plane mirror 322 is applied to a segmented mirror array 324 shown in more detail in FIG. 3b. Light reflected from the array 324 impinges on the photoelectric diode array 326 which produces outputs detected by detector electronics 328.

The optical processing performed by the optical elements between the first slit 300 and the segmented mirror array 324 is readily understood by those skilled in the art. Suffice it to say that, as shown schematically in FIG. 3b, at the input to segmented mirror array 324, the light incident on the slit 300 has been separated into plural vertically separated spectral orders, each of which is formed of a limited continuous spectrum of increasing wavelengths, with the maximum wavelength, for example, of the $k^{th}$ spectral order being substantially continuous, in Angstroms, with the minimum wavelength of the next high spectral order $k+1$.

As shown in FIG. 3b, the segmented mirror array 324 includes plural segmented mirrors 330, each having a reflective surface 332 for reflecting incoming light from the folded optics 322, 320, 318 and Echelle grating 316. Each mirror 330 includes a pair of parts $330_1$ and $330_2$ integrally joined at a narrow part $330_3$ and is made of a material, such as stainless steel, aluminum, plastic, etc., which enables elastic deformation and thus selection of the relative positioning of the parts $330_1$ and $330_2$ by means of mirror tilt and lock screw set 334. Adjustment of the tilt and lock screw set 334 permits selective adjustment of the angle of inclination of the respective reflecting surface 332, whereby it is possible to select any spectral order of the incoming light for reflection to, and subsequent analysis by, the photoelectric diode array 326 and detector electronics 328.

Further, by selecting the spacing $l_1$ between adjacent mirror segments 330, according to the invention, a selected range of wavelengths along the wavelength axis of the spectral order selected by means of the tilt and lock screw set 334 is selected. The range of selected wavelengths of the selected spectral order depends on the width $l_2$ of the reflective surface 332 of the mirror segments 330, which in turn is also selectable. Spacing between adjacent mirror segments can be established and fixed by means of spacers or other conventional means. The width of the reflective surface 332 can be selected either by means of selection of the width of the mirror 330 itself, or by appropriate treatment of portions of the reflective surface with a non-reflecting substance to define a reflecting width as needed. In this way, in each of the spectrographs $24_1$, $24_2$, a full spectral range of 1850–9000 Å is covered. This very wide spectral response obtained by means of a single set of a spectrograph and a gated, intensified photoelectric diode array detector makes it possible to determine the concentration of all elements simultaneously within 1 minute and thus the elemental composition of molten metal alloys.

Figure 2:
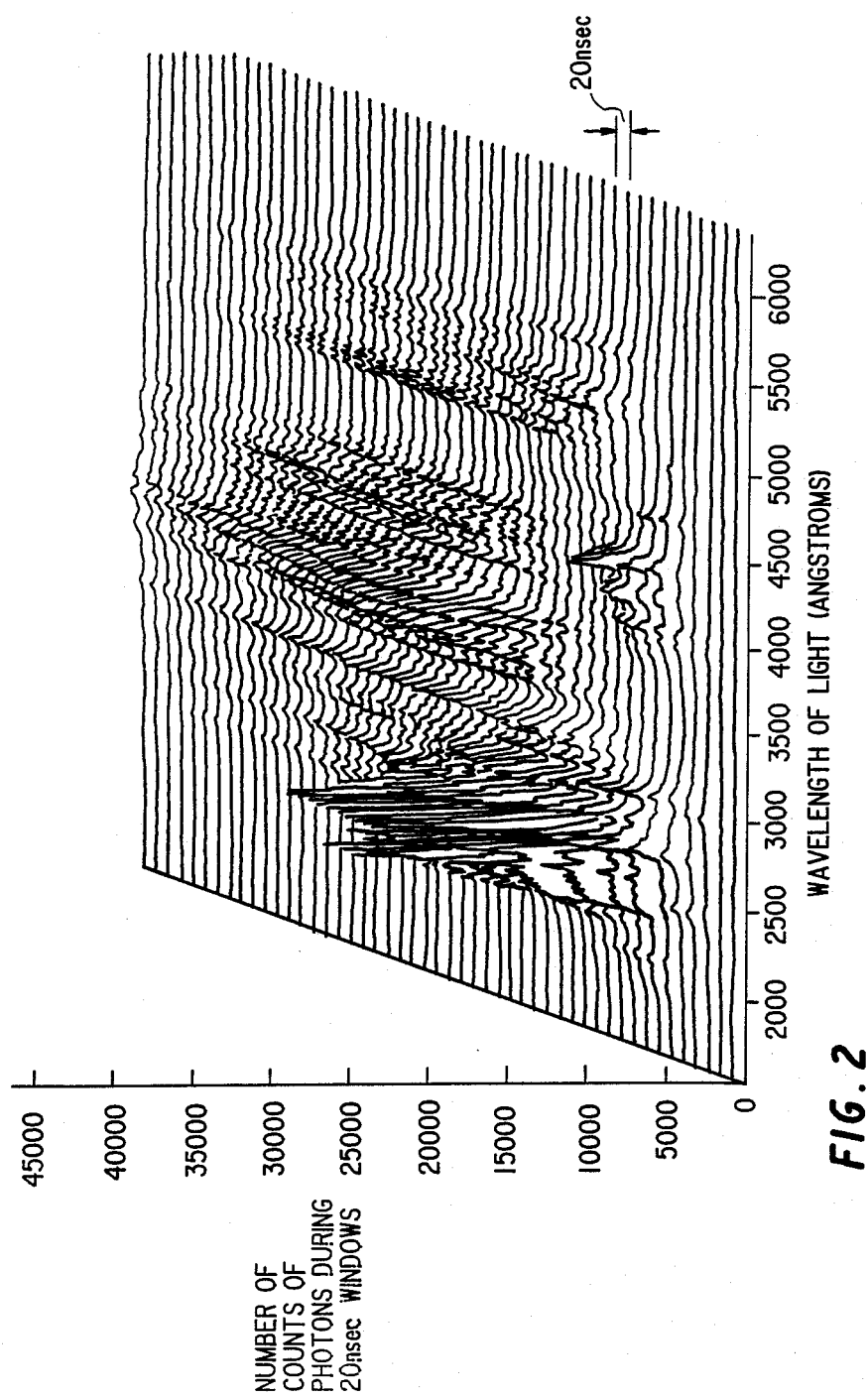
FIG. 2 is a waveform diagram illustrating a sequence of spectral emissions derived at 20 nsec intervals from a typical molten metal upon irradiation by the pulsed laser of the invention.

The spectrographs $24_1$ and $24_2$ are used to perform time-resolved spectroscopic measurements of the emissions from the plasma plume during the first and second time windows above discussed. The time-resolved spectroscopic measurements of the invention are based on the recognition that the plasma produced by the pulsed laser beam evolves as a series of competing plasma, atomic and fluid dynamical processes which emerge and fade away in succession. This aspect of the laser produced plasma is shown in FIG. 2. In recognition of the evolutionary nature of the plasma, it is further recognized that simple-minded time integration as practiced in the prior art leads to misleading and erroneous results which destroy the cause and effect relationship of the emission (or absorption) intensity at a wavelength and the concentration of the elemental species designated by that wavelength. Thus, the spectroscopic measurements of Applicants' invention are time-resolved, i.e., taking place during short time intervals as brief as 5 nsec for proper interpretation of the intensity data. To that end, the spectrographs employ a gated channel plate coupled to the above-noted photodiode array 326.

As is evident from the above description, several measures are employed to optimize the spectroscopic measurement according to the present invention. First, as shown in FIG. 3a, between the Echelle grating 316 and the photodiode array 326, there is provided "folded optics" in the form of plural mirrors 318, 320 and 322 which produce plural reflections of the spectra so that the spectra travel increased distances and thereby are further separated to increase resolution at the detector array. A second measure is the provision of the segmented mirror array 324 having segmented mirrors 330 which are selectively adjusted so that only desired regions of the incoming spectrum are reflected toward selected detector elements, i.e., pixels, of the detector array 326. The controllable segmented mirrors 330 thus are employed to eliminate spectral region which are known not to have spectra of interest so that maximum utilization of the available detecting elements of the gated array are used in the detection of only spectra segments of interest. The folded optics and individually controllable segmented mirror assembly permits high resolution detection of 20 or more emission line profiles with one gated, intensified photodiode array detector. The photodiode array detector may consist of 1024 detecting elements or more for this application.

In addition to being time-resolved, the spectroscopic measurement of the emissions from the plasma plume is also spatially resolved according to the present invention. By way of elaboration, it has been determined according to the present invention that the temperature, the vapor-phase elemental number density and the degrees of ionization of each species within the plasma plume are strong functions of a position in reference to the molten metal surface and the laser beam axis. Such spatial dependence leads to regions that are optically thick and those that are optically thin, and the regions of such different spectroscopic properties must be separated in order to obtain tractable data.

The probe 10 of the present invention incorporates spatially-resolved coupling of the plasma emission to the entrance slit of each spectrograph. To that end, the optics block 16, which includes a total of five lenses (one for application of the laser beam, two for range-finding and one each for application of light to the spectrographs 241, 242), at the leading end of the probe 18 includes a lens which provides spatially-resolved coupling of the plasma emissions to the entrance slit of each spectrograph. For instance, in the case of the atomic line image and spectrum from the plasma plume produced in a vacuum furnace, the optimal region of the plasma is located 1.5 ± 0.5 mm away from the surface of the molten metal and 2 ± 0.5 mm from the laser beam axis at 350 nsec after the initiation of the laser pulse. Thus, for a spectroscopic measurement in on of the a vacuum taken at 350 nsec after initiation of the laser pulse, according to the present invention the lens of the optics block is designed and positioned to focus 1.5 mm away from the surface of the molten metal and 2 mm from the laser beam axis.

In order to assure that the focal spot of the laser beam on the surface of the molten metal is of the requisite size, and in order to assure that a valid spatially resolved spectroscopic measurement is performed, the distance from that lens of the optics block 16 dedicated to the respective spectrograph and focusing the pulsed laser beam from the laser 14 must be precisely set before firing the laser 14. To that end, the present invention employs the rangefinder 22 resident within the probe 10. The rangefinder 22 controls the placement of the target metal melt surface by regulating the pressure of an inert gas applied via the probe to the immersed end 18 of the probe while the end 18 of the probe is immersed in the molten metal. The rangefinder 22 utilizes an autocollimation technique employing a diode laser 30 and a detector 32 in the form of phototransistor pair. The rangefinder 22 detects the approach (or retreat) of the molten metal surface in dependence upon the size of a spot emitted by the diode laser on the phototransistor pair after reflection of the diode laser beam from the surface of the molten metal. When the molten metal surface is presented at a predetermined distance from the high power laser 14, the rangefinder 22 automatically issues an electronics command indicative of that fact to enable outputting of the laser 14. Throughout, the rangefinder controls the inert gas pressure applied via the immersed end of the probe 10 to establish the requisite distance of the molten metal from the laser 14.

In selecting a diode laser for the rangefinder 22, a key characteristic of the diode laser 30 is that it have a brightness greater than the background of the molten metal. The detector on the other hand must be able to see only the wavelength of the signal emitted by the diode laser, and thus needs narrow range filtering of the incoming light from the molten metal and from the diode laser. As the distance in the optical path between the diode laser 30 and the molten metal surface and that between the surface and the detector 32 increases the focal spot of the beam emitted by the diode laser 30 and focused on the surface increases, resulting in a decrease in the intensity detected by the detector 32 at the wavelength of the diode laser 30. Similarly, as the distance between the diode laser 30 and the molten metal surface and that between the surface and the detector 32 becomes shorter, then the detected intensity increases as the focal spot of the laser beam from the diode laser 30 decreases in size on the molten metal surface. In this way, using the standard autocollimation technique, it is possible to obtain from the detector 32 a signal which is indicative of the distance between the focusing lens for the high power laser 14 and the surface of the molten metal.

To facilitate the detection of the laser beam from the diode laser 30, which operates at near infrared wavelength, by the detector 32, the beam emitted by the diode laser 30 is encoded by a narrow frequency, e.g. 500 Hz. To that end, the current applied to the diode laser 30 is modulated at a 500 Hz rate to amplitude modulate the laser beam produced by the diode laser 30 at a 500 Hz rate. The detector 32 then includes a decoding 500 Hz filter and detector (not shown) for detecting the 500 Hz amplitude modulation of the laser beam from the diode laser 30. The amplitude of the demodulated 500 Hz signal is then used to determine the range under investigation. In this way, the present invention achieves additional selectivity of the laser beam from the diode laser 30 with respect to the radiation produced by the molten metal as seen by the detector 32.

Optionally, another rangefinder (not shown), a coupled cavity laser interferometer employing the surface of the molten metal as a third reflector, is also used in the event that extremely precise rangefinding is essential. The coupled cavity laser interferometer, as is well known, employs a laser having two mirrors with a light generating source pumping light into the region between the two mirrors. The output of this laser is light leaking from one of the two mirrors, i.e., trapped light in the cavity of the laser is lost resulting in a decrease in the gain of the laser. The more light that is trapped in the cavity, the greater is the amplification or gain given to light passing through the laser cavity. By pumping back leaking light into the laser cavity, it is possible either to increase or decrease the gain in dependence upon the phase relationship of the leaking light pumped back into the laser cavity with respect to the recirculating light existing in the laser cavity. In the coupled cavity laser interferometer serving as a rangefinder according to the present invention, the leakage light is directed to the molten metal surface and reflected therefrom back to the laser cavity. In dependence upon the phase of the reflected light entering the laser cavity, the intensity of the laser field within the primary cavity of the laser changes and this principle is used to determine within a fraction of a wavelength the range between the coupled cavity laser interferometer (not shown) and the surface of the molten metal.

If a coupled cavity laser interferometer is employed, the laser beam therefrom is directed down toward the focusing lens of the optics block 16 slightly off axis with respect to that of the laser 14. The exact placement of the molten metal surface is detected at that point corresponding to the point of maximum gain modulation of the laser due to the retroreflected laser light from the target surface. When used with the autocollimator rangefinder 22, the two rangefinders are used in a complementary manner. However, in view of the relatively large spot produced by the laser 14 at the molten metal surface and in view of the substantial accuracy in rangefinding enabled by means of the autocollimator rangefinder 22, it is anticipated that it will be unnecessary to provide a coupled-cavity laser interferometer in addition to the autocollimation rangefinder 22 except for rare circumstances.

In order to evaluate the spectral pattern detected by the spectrographs $24_1$, $24_2$, the present invention employs spectral pattern recognition processing. The processing of the invention is based on the recognition that alloys such as different types of steel generally consist of 10 or 15 different elements at varying concentrations. Such abundance of species contributes to complexities of the emissions spectra, leading to the so-called inter-elemental interferences. The intensity and spectral profile of an emission line, characteristic of an element in the electrically neutral state, may be influenced by appearance of another emission line belonging to another element present in the alloy.

The prior art of analytical spectroscopy is that a photodetector is positioned at a fixed location on the image plane of the spectrograph and such an interference contributes to an erroneous measurement of the line intensity and an incorrect determination of the concentration of the element. The processing of the present invention determines the intensity profile of a spectral region in the immediate neighborhood of the emission line of interest, determines the extent of interference, and removes it from the line intensity before further processing by an elemental concentration calibration scheme. The pattern recognition processing identifies the interfering line center profiles by means of iterative application of guess and confirm computation routine, typically involving a maximum of 3 to 5 iterations. The incorporation of such powerful processing according to the present invention is made possible by the use of the gated channel plate intensifier in conjunction with a photodiode array detector. Next described in more detail is the spectral pattern recognition processing performed according to the invention.

Figure 4:
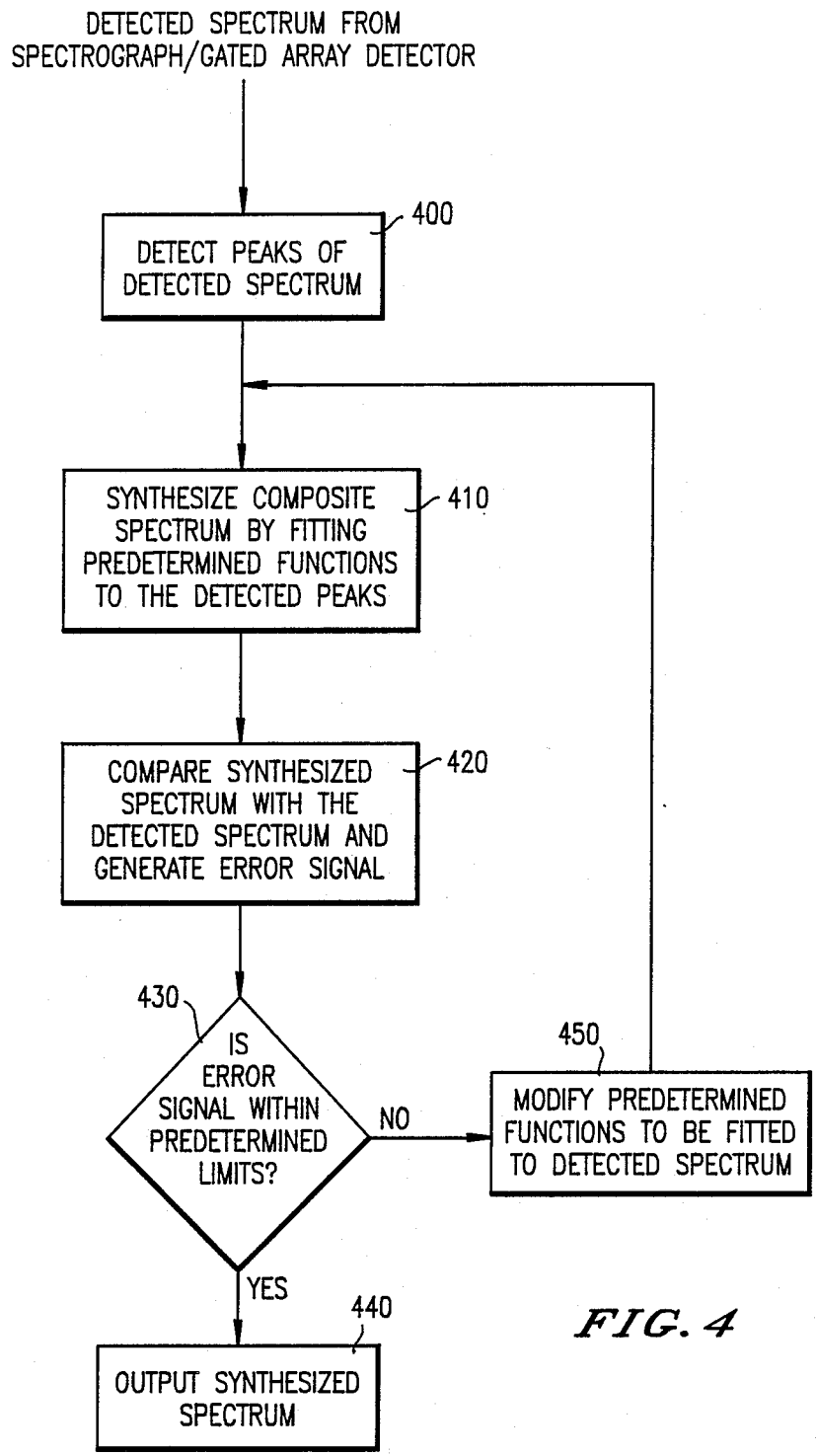
FIG. 4 is a flow chart illustrating the iterative processing steps performed in the spectral analysis of the invention.

Referring to FIG. 4, the spectral pattern recognition processing begins by taking the experimental spectral profile detected by the array detector and decomposing it into individual spectral lines to determine the locations and amplitudes of the peaks of the profile, as indicated in step 400 of FIG. 4. Then, in step 410 of FIG. 4, the processing synthesizes a spectrum on the basis of the location and size of the peaks detected at the output of the photodiode array detector. Synthesis of the spectrum is performed by fitting a predetermined function, such as a Gaussian function or a Lorentzian function, or a hybrid thereof as derived for example from a convolution of these two functions, to each peak detected in the step 410. The width of each function fitted to each peak is predetermined. In step 420, the synthesized spectrum is completed by mapping the so derived functions onto the corresponding frequency regions, with areas of overlap between different functions being added where overlap occurs. Then, in the step 430, the synthesized spectrum is compared with the original spectrum at the output of the detector array to derive an error signal as the difference therebetween. The error signal is checked to determine if it is greater or lesser than a predetermined limit in step 440. If so, in a step 440, the error signal is used to change the functions applied to each peak of the original spectrum, for example to decrease or increase the amplitude or decrease or increase the width of such functions, at each detected peak. The processing then returns to step 410 where a new synthesized spectrum is derived based on the modified functions corrected by means of the previously derived error signals. Step 420 is then repeated and a new error signal is then obtained. Step 430 is then repeated and it is determined whether or not the new error signal is within predetermined limits. If not, the processing returns to step 410 and is repeated, i.e. a new synthesized spectrum is derived and a new error signal obtained. If the error signal is within predetermined limits, indicating that the processing has converged within acceptable limits, the processing is ended and the synthesized spectrum, which is then determined to be an accurate representation of the spectrum actually detected by the spectrographic detector array, is output in step 450.

A further consideration in implementing the present invention is the calibration of the spectrographs for molten metal analysis. The calibration procedure of each spectrograph begins by applying light of a predetermined wavelength typically at the edge of the spectral region of interest, to the spectrograph and controlling the positioning of one of the segmented mirrors so that the light of predetermined wavelength is incident on selected pixels of the detector array. A second light source of different predetermined wavelength is then used to emit light to the spectrograph, and a second segmented mirror is controlled to reflect the second wavelength to another group of detector elements of the detector array. Since the relative positioning of the segmented mirrors are known, and since the spectral width of light reflected by the segmented spectral mirrors is known, it is possible to obtain a coarse calibration of the spectral equipment. Fine calibration of the segmented mirrors is then achieved by obtaining an emission spectrum from a metal of known composition, and comparing the detected spectrum from the metal of known composition with that actually detected at the detector array.

It is anticipated that an on-going calibration will be performed during molten metal analysis. In this on-going calibration, spectroscopic measurements of the molten metal will be performed and spectroscopic responses according to the individual elements first obtained. Samples of the molten metal are then taken at the same time of each laser pulse measurement. After the samples are cooled and solidified, they are analyzed by a conventional means of atomic emission spectroscopy and x-ray fluorescence, with the resulting compositions then being used as standards for the molten metal analysis by the laser produced plasmas.

FIG. 5 provides an expanded illustration of probe 10 of the invention in relation to the molten metal under investigation, and further illustrates the connection of the probe 10 to a control console 500 by means of the umbilical cord 19. The console 500 houses a dedicated microcomputer 510, a fast digitizer and buffer 520, time trigger pulse generators 530, cooling water flow regulator 540, electronically operated pressure and flow regulators 550 for inert gas supply, the electronics for the rangefinders 560, a power supply 570, and storage capacitor bank 580 for the laser 14. Since each of the individual elements of the control console 500 is in of itself conventional, no further description thereof is provided.

FIG. 5 is of interest because it schematically illustrates the control of the probe 10 by the control console 500 and the positioning thereof relative to the molten metal under investigation. With such a configuration, as above described, the laser 14 can be fired more than once in 1 minute and the resulting data can be analyzed for determination of the elemental composition within 1 minute of each laser firing.

FIG. 5 further illustrates the separation of the probe 10, where all excitation and measurements take place, from the control console 500, where the probe performance is monitored and spectroscopic data are analyzed for determination of elemental composition. As illustrated in FIG. 5, the linkage between the two is accomplished through the flexible hermetically-sealed umbilical cord 19 containing all electrical, pneumatic, coolant and gas lines. This configuration enables operation of the probe both in vacuum furnaces and in those operating in ambient temperature. Such environments typically require distinctly different modes of operation, yet the method and apparatus of the present invention are applicable to both.

The present invention enjoys distinct advantages in that according to the present invention there is no need for contact between the molten metal and the diagnostic elements. Further, obtaining the two spectra in extremely brief measurement times of less than 1 $\mu$sec is possible. Timing and detector electronics are well suited for computer supervision of the entire measurement protocol and for analysis of data. While a single shot run is sufficient for composition analysis, several runs can be taken within 1 minute for improved statistics if needed, and the technique offers a very wide margin for extensions, improvement and variations in its applications because of the physics and technology can offer a good deal more information than is called for at present.

Obviously, numerous modifications and variations of the present invention are possible in light of the above teachings. It is therefore to be understood that within the scope of the appended claims, the invention may be practiced otherwise than as specifically described herein.

WHAT IS CLAIMED AS NEW AND DESIRED TO BE SECURED BY LETTERS PATENT OF THE UNITED STATES IS:

1. A method for spectroscopic analysis of a molten metal, comprising:
    providing a probe including a casing having an open end adapted to be immersed in the molten metal, laser means disposed in said casing for irradiating the surface of the molten metal adjacent the open end with a laser beam of predetermined energy density and focal spot size, and spectroscopic detector means disposed in said casing for detecting spectral components of light emitted from a plasma produced by the laser means;
    immersing the open end of the casing into the molten metal;
    irradiating the molten metal with a laser beam from said laser means to produce a plasma representative of the composition of the molten metal, said irradiating being performed during immersion of the casing open end into the molten metal; and
    detecting spectral components of radiation emitted by the plasma by means of the spectroscopic detector means in the casing and producing signals corresponding to the detected spectral components.

2. The method according to claim 1, wherein:
    said irradiating step comprises irradiating said molten metal with a pulsed laser beam; and
    said detecting step comprises detecting spectral line reversals in radiation emitted by said plasma during a predetermined first time window shortly after said pulsed laser beam reaches peak power and prior to said plasma reaching thermal equilibrium.

3. The method according to claim 1, wherein said detecting step comprises:
    detecting spectral components in the radiation emitted by said plasma during a predetermined time window in an afterglow period during which said plasma is in thermal equilibrium.

4. The method according to claim 2, wherein said detecting step comprises:

detecting spectral components in the radiation emitted by said plasma during a predetermined second time window in an afterglow period during which said plasma is in thermal equilibrium.

5. The method according to claims 1, 2, 3 or 4, wherein said irradiating step comprises:
irradiating said molten metal with a pulsed laser beam having substantially triangular waveshape with a rise time of 50 ± 20 nsec, a time duration of 50–100 nsec at the halfwidth, a power density greater than $10^9$ W/cm$^2$, and a focal spot size of 1–4 mm$^2$ on the surface of the molten metal.

6. The method according to claim 2, wherein said first time window has a time duration of 5–50 nsec and begins 50–500 nsec after the pulsed laser beam reaches peak power.

7. The method according to claims 3, wherein said predetermined time window has a time duration of 20–500 nsec and begins between 250 nsec and 5 $\mu$sec after initiation of said irradiating step.

8. The method according to claim 4, wherein said first time window has a time duration of 5–50 nsec and begins 50–500 nsec after the pulsed laser beam reaches peak power.

9. The method according to claim 8, wherein said second time window has a time duration of 20–500 nsec and begins between 250 nsec and 5 $\mu$sec after initiation of said irradiating step.

10. The method according to claims 1, 2, 3 or 4, comprising:
said providing step comprising providing rangefinder means disposed in said casing for detecting the distance between the surface of the molten metal and a focusing lens of said laser means;
introducing an inert gas under pressure into a space between the focusing lens and the surface of the molten metal;
detecting the distance between the surface of the molten metal and the focusing lens using said rangefinding means; and
controlling the pressure of the inert gas introduced into said space based on the detected distance between the surface of the molten metal and the focusing lens so that said distance between the surface of the molten metal and the focusing lens is maintained at a predetermined distance.

11. The method according to claim 10, comprising:
performing said irradiating step only when the surface of said molten metal is detected to be at said predetermined distance from said focusing lens.

12. The method according to claim 9, comprising:
said providing step comprising providing rangefinder means disposed in said casing for detecting the distance between the surface of the molten metal and a focusing lens of said laser means;
introducing an inert gas under pressure into a space between the focusing lens and the surface of the molten metal;
detecting the distance between the surface of the molten metal and the focusing lens using said rangefinding means; and
controlling the pressure of the inert gas introduced into said space based on the detected distance between the surface of the molten metal and the focusing lens so that said distance between the surface of the molten metal and the focusing lens is maintained at a predetermined distance.

13. The method according to claim 12, comprising:
performing said irradiating step only when the surface of said molten metal is detected to be at said predetermined distance from said focusing lens.

14. The method according to claim 11, wherein said step of detecting spectral components is performed in relation to a predetermined region of the plasma at a first predetermined distance of the surface of the molten metal and a second predetermined distance away from the optical axis of said laser means.

15. The method according to claim 14, wherein said first predetermined distance is 1.5 ± 0.5 mm and said second predetermined distance is 2.0 ± 0.5 mm.

16. The method according to claims 1, 2, 3 or 4 comprising:
detecting, based on the spectral components detected in said detecting step, peaks in the spectrum represented by the detected spectral components;
fitting a predetermined function to each detected peak;
forming a synthesized composite spectrum based on the fitted step;
comparing the synthesized composite spectrum with the spectrum represented by the detected spectral components and producing an error signal based on the difference therebetween; and
determining whether the error signal is within predetermined limits, and if so, outputting the synthesized composite spectrum as representative of the constituent emission lines of the elements in the molten metal, and if not, modifying the functional fit to each detected peak and iteratively repeating said fitting, comparing and determining steps until said error signal is within said predetermined limits.

17. The method according to claim 9, comprising:
detecting, based on the spectral components detected in said detecting step, peaks in the spectrum represented by the detected spectral components;
fitting a predetermined function to each detected peak;
forming a synthesized composite spectrum based on the fitted step;
comparing the synthesized composite spectrum with the spectrum represented by the detected spectral components and producing an error signal based on the difference therebetween; and
determining whether the error signal is within predetermined limits, and if so, outputting the synthesized composite spectrum as representative of the constituent emission lines of the elements in the molten metal, and if not, modifying the functional fit to each detected peak and iteratively repeating said fitting, comparing and determining steps until said error signal is within said predetermined limits.

18. The method according to claims 16, comprising:
detecting, based on the spectral components detected in said detecting step, peaks in the spectrum represented by the detected spectral components;
fitting a predetermined function to each detected peak;
forming a synthesized composite spectrum based on the fitted step;
comparing the synthesized composite spectrum with the spectrum represented by the detected spectral components and producing an error signal based on the difference therebetween; and
determining whether the error signal is within predetermined limits, and if so, outputting the synthesized composite spectrum as representative of the constituent emission lines of the elements in the molten metal, and if not, modifying the functional fit to each detected peak and iteratively repeating said fitting, comparing and determining steps until said error signal is within said predetermined limits.

19. The method according to claim 1, wherein said irradiating step comprises:
irradiating the surface of the molten metal with a pulsed laser beam having a waveshape, time duration, focal spot size and energy density selected such that the evaporation of said molten metal into said plasma substantially coincides with a thermal diffusion front produced by said laser beam in the molten metal.

20. The method according to claim 5, wherein said irradiating step comprises:
irradiating the surface of the molten metal with a pulsed laser beam having a waveshape, time duration, focal spot size and energy density selected such that the evaporation of said molten metal into said plasma substantially coincides with a thermal diffusion front produced by said laser beam in the molten metal.

21. The method according to claim 1, wherein said casing comprises a protective shell housing said laser means and said spectroscopic detector means, and a refractory sheath fitted to said protective shell and defining said open end of said casing, said method further comprising:
said immersing step comprising immersing only said refractory sheath into the molten metal; and
cooling said protective shell during immersing of said refractory sheath in the molten metal.

22. An apparatus for spectroscopic analysis of a molten metal, comprising:
a probe comprising a casing having an open end adapted to be immersed in the molten metal;
laser means disposed in said casing for irradiating the surface of the molten metal adjacent to the open end of the casing with a laser beam so as to produce a plasma having a composition representative of the composition of the molten metal; and
spectroscopic detecting means disposed in said casing and optically coupled to the plasma for detecting spectral components of radiation emitted by the plasma and producing signals corresponding to the detected spectral components.

23. The apparatus according to claim 22, wherein:
said laser means comprises a Q-switched laser which generates a pulsed laser beam; and
said spectroscopic detecting means comprises first means for detecting spectral line reversals in radiation emitted by said plasma during a predetermined first time window shortly after said pulsed laser beam reaches peak power and prior to said plasma reaching thermal equilibrium.

24. The apparatus according to claim 22, wherein said spectroscopic detector means comprises:
means for detecting spectral components in the radiation emitted by said plasma during a predetermined time window in an afterglow period during which said plasma is in thermal equilibrium.

25. The apparatus according to claim 23, wherein said spectroscopic detecting means comprises:
second means for detecting spectral components in the radiation emitted by said plasma during a predetermined second time window in an afterglow period during which said plasma means is in thermal equilibrium; and
said first and second means detecting spectral components in said first and second time windows, respectively, for each pulsed laser beam generated by said laser.

26. The apparatus according to claims 22 or 23, wherein said laser means comprises:
a Q-switched laser and a focusing lens which in combination produces at the surface of said molten metal a pulsed laser beam having substantially triangular waveshape with a rise time of 50 ± 20 nsec, a time duration of 50–100 nsec at the halfwidth, a power density greater than $10^9$ W/cm$^2$, and a focal spot size of 1–4 mm$^2$ on the surface of the molten metal.

27. The apparatus according to claims 23 or 25, wherein said laser means comprises:
a focusing lens which in combination with said Q-switched laser produces at the surface of the molten metal said molten metal a pulsed laser beam having substantially triangular waveshape with a rise time of 50 ± 20 nsec, a time duration of 50–100 nsec at the halfwidth, a power density greater than $10^9$ W/cm$^2$, and a focal spot size of 1–3 mm on the surface of the molten metal.

28. The apparatus according to claim 23, wherein said first time window has a time duration of 5–50 nsec and begins 50–500 nsec after the pulsed laser beam reaches peak power.

29. The apparatus according to claim 24, wherein said predetermined time window has a time duration of 20–500 nsec and begins between 250 nsec and 5 μsec after initiation of said irradiating step.

30. The apparatus according to claim 25, wherein said first time window has a time duration of 5–50 nsec and begins 50–500 nsec after the pulsed laser beam reaches peak power.

31. The apparatus according to claim 30, wherein said second time window has a time duration of 20–500 nsec and begins between 250 nsec and 5 μsec after initiation of said irradiating step.

32. The apparatus according to claims 22 or 24, further comprising:
means introducing an inert gas under pressure into a space between a focusing lens of the laser means and the surface of the molten metal;
rangefinder means disposed in the casing for detecting the distance between the surface of the molten metal and the focusing lens; and
means for controlling the pressure of the inert gas introduced into said space based on the detected distance between the surface of the molten metal and the focusing lens so that said distance between the surface of the molten metal and the focusing lens is maintained at a predetermined distance.

33. The apparatus according to claim 32, comprising:
means for actuating said laser means only when the surface of said molten metal is detected by said rangefinder means to be at said predetermined distance from said focusing lens.

34. The apparatus according to claim 31, further comprising:
means for introducing an inert gas under pressure into a space between a focusing lens of the laser means and the surface of the molten metal;

21 rangefinder means disposed in the casing for detecting the distance between the surface of the molten metal and the focusing lens; and means for controlling the pressure of the inert gas introduced into said space based on the detected distance between the surface of the molten metal and the focusing lens so that said distance between the surface of the molten metal and the focusing lens is maintained at a predetermined distance.

35. The method according to claim 34, comprising:
means for activating said laser means only when the surface of said molten metal is detected to be at said predetermined distance from said focusing lens.

36. The apparatus according to claim 34, wherein said spectroscopic detecting means comprises:
a spectrograph; and
focusing means for focusing light applied to said spectrograph and produced in a predetermined region of the plasma at a first predetermined distance from the surface of the molten metal and a second predetermined distance away from the optical axis of said laser means.

37. The apparatus according to claim 36, wherein said first predetermined distance is 1.5 ± 0.5 mm and said second predetermined distance is 2.0 ± 0.5 mm.

38. The apparatus according to claims 22 or 24, comprising:
processing means for processing the signals produced by said spectrograph detecting means by performing the following functions,
means for detecting, based on the spectral components detected by said spectroscopic detecting means, peaks in the spectrum represented by the detected spectral components,
means for fitting a predetermined function to each detected peak,
means for forming a synthesized composite spectrum based on the fitted function,
means for comparing the synthesized composite spectrum with the spectrum represented by the detected spectral components and producing an error signal based on the difference therebetween, and
means for determining whether the error signal is within predetermined limits, and if so, outputting the synthesized composite spectrum as representative of the emission lines of the constituent elements in the molten metal, and if not, modifying the functional fit to each detected peak and alternatively repeating said fitting, comparing and determining functions until said error signal is within said predetermined limits.

39. The apparatus according to claims 23 or 25, further comprising:
processing means for processing the signals produced by said spectrograph detecting means by performing the following functions,
means for detecting, based on the spectral components detected said spectroscopic detecting means, peaks in the spectrum represented by the detected spectral components,
means for fitting a predetermined function to each detected peak,
means for forming a synthesized composite spectrum based on the fitted function,
means for comparing the synthesized composite spectrum with the spectrum represented by the detected spectral components and producing an error signal based on the difference therebetween, and

22 means for determining whether the error signal is within predetermined limits, and if so, outputting the synthesized composite spectrum as representative of the emission lines of the constituent elements in the molten metal, and if not, modifying the functional fit to each detected peak and alternatively repeating said fitting, comparing and determining functions until said error signal is within said predetermined limits.

40. The apparatus according to claim 31, further comprising:
processing means for processing the signals produced by said spectrograph detecting means by performing the following functions,
means for detecting, based on the spectral components detected in said spectroscopic detecting means, peaks in the spectrum represented by the detected spectral components,
means for fitting a predetermined function to each detected peak,
means for forming a synthesized composite spectrum based on the fitted function,
means for comparing the synthesized composite spectrum with the spectrum represented by the detected spectral components and producing an error signal based on the difference therebetween, and
means for determining whether the error signal is within predetermined limits, and if so, outputting the synthesized composite spectrum as representative of the emission lines of the constituent elements in the molten metal, and if not, modifying the functional fit to each detected peak and alternatively repeating said fitting, comparing and determining functions until said error signal is within said predetermined limits.

41. The apparatus according to claim 34, further comprising:
processing means for processing the signals produced by said spectrograph detecting means by performing the following functions,
means for detecting, based on the spectral components detected in said spectroscopic detecting means, peaks in the spectrum represented by the detected spectral components,
means for fitting a predetermined function to each detected peak,
means for forming a synthesized composite spectrum based on the fitted function,
means for comparing the synthesized composite spectrum with the spectrum represented by the detected spectral components and producing an error signal based on the difference therebetween, and
means for determining whether the error signal is within predetermined limits, and if so, outputting the synthesized composite spectrum as representative of the emission lines of the constituent elements in of the molten metal, and if not, modifying the functional fit to each detected peak and alternatively repeating said fitting, comparing and determining functions until said error signal is within said predetermined limits.

42. The apparatus according to claim 22, wherein said laser means comprises:
a Q-switched laser and a focusing lens which in combination produce at the surface of the molten metal a pulsed laser beam having a waveshape, time duration, focal spot size and energy density selected such that the evaporation of said molten metal into said plasma substantially coincides with a thermal diffusion front produced by said laser beam in the molten metal.

43. The apparatus according to claim 41, wherein said laser means comprises:
a Q-switched laser and a focusing lens which in combination produce at the surface of the molten metal a pulsed laser beam having a waveshape, time duration, focal spot size and energy density selected such that the evaporation of said molten metal into said plasma substantially coincides with a thermal diffusion front produced by said laser beam in the molten metal.

44. The apparatus according to claims 22 or 24, wherein said spectroscopic detecting means comprises:
means for separating radiation emitted from said plasma into plural spectral components;
a gated array of photodetecting pixel elements optically coupled to said radiation separating means to detect the presence of predetermined spectral components; and
selection means, including plural segmented mirrors, for selectively reflecting selected of said spatially separated spectral components to selected of said pixel- elements.

45. The apparatus according to claims 23 or 25, wherein said spectroscopic detecting means comprises:
means for separating radiation emitted from said plasma into plural spectral components;
a gated array of photodetecting pixel elements optically coupled to said radiation separating means to detect the presence of predetermined spectral components; and
selection means, including plural segmented mirrors, for selectively reflecting selected of said spatially separated spectral components to selected of said pixel, elements.

46. The apparatus according to claim 31, wherein said spectroscopic detecting means comprises:
means for separating radiation emitted from said plasma into plural spectral components;
a gated array of photodetecting pixel elements optically coupled to said radiation separation means to detect the presence of predetermined spectral components; and
selection means, including plural segmented mirrors, for selectively reflecting selected of said spatially separated spectral components to selected of said pixel elements.

47. The apparatus according to claim 41, wherein said spectroscopic detecting means comprises:
means for separating radiation emitted from said plasma into plural spectral components;
a gated array of photodetecting pixel elements optically coupled to said radiation separation means to detect the presence of predetermined spectral components; and
selection means, including plural segmented mirrors, for selectively reflecting selected of said spatially separated spectral components to selected of said pixel elements.

48. The apparatus according to claim 44, further comprising:
folded optics means, provided between said radiation separating means and said selection means, including plural mirrors, for reflecting the spectral components separated by said separating means plural times thereby to increase the distance travelled by said spectral components and the spatial separation thereof.

49. The apparatus according to claim 45, further comprising:
folded optics means, provided between said radiation separating means and said selection means, including plural mirrors, for reflecting the spectral components separated by said separating means plural times thereby to increase the distance travelled by said spectral components and the spatial separation thereof.

50. The apparatus according to claim 47, further comprising:
folded optics means, provided between said radiation separating means and said selection means, including plural mirrors, for reflecting the spectral components separated by said separating means plural times thereby to increase the distance travelled by said spectral components and the spatial separation thereof.

51. The apparatus according to claim 47 further comprising:
folded optics means, provided between said radiation separating means and said selection means, including plural mirrors, for reflecting the spectral components separated by said separating means plural times thereby to increase the distance travelled by said spectral components and the spatial separation thereof.

52. The apparatus according to claim 22, further comprising:
said casing comprising a protective shell housing said laser means and said spectroscopic detecting means, and a refractory sheath fitted to said protective shell and defining said open end of said casing and adapted to be immersed in the molten metal; and
cooling means for cooling said protective shell during immersing of said refractory sheath in the molten metal.

* * * * *

REEXAMINATION CERTIFICATE (2928th)
United States Patent [19]
Kim

[11] B1 4,986,658
[45] Certificate Issued Jun. 25, 1996

[54] TRANSIENT SPECTROSCOPIC METHOD AND APPARATUS FOR IN-PROCESS ANALYSIS OF MOLTEN METAL

[75] Inventor: Yong W. Kim, Bethlehem, Pa.

[73] Assignee: Lehigh University, Bethlehem, Pa.

Reexamination Request:
No. 90/003,696, Jan. 20, 1995

Reexamination Certificate for:
Patent No.: 4,986,658
Issued: Jan. 22, 1991
Appl. No.: 341,748
Filed: Apr. 21, 1989

[51] Int. Cl.$^6$ .............. G01J 3/443; G01J 3/18; G01N 21/63
[52] U.S. Cl. .............. 356/318; 356/328; 356/334
[58] Field of Search .............. 356/318; 73/DIG. 9

[56] References Cited

U.S. PATENT DOCUMENTS

| | | |
|---|---|---|
| 3,645,628 | 2/1972 | Bojic et al. . |
| 4,182,574 | 1/1980 | Quillfeldt .............. 356/318 |
| 4,645,342 | 2/1987 | Tanimoto et al. .............. 356/318 |
| 4,652,128 | 3/1987 | Tsunoyama et al. .............. 356/318 |

FOREIGN PATENT DOCUMENTS

| | | |
|---|---|---|
| 176625 | 4/1986 | European Pat. Off. . |
| 52-154690 | 12/1977 | Japan . |
| 56-114746 | 9/1981 | Japan . |
| 61-181947 | 8/1986 | Japan . |
| 62-188919 | 8/1987 | Japan . |
| 62-282247 | 12/1987 | Japan .............. 356/318 |
| 2154315 | 9/1985 | United Kingdom . |

OTHER PUBLICATIONS

"Intelligent Processing of Materials and Advanced Sensors," by Yong W. Kim, Symposium Proceedings, Fall 1986, Orlando, FL, pp. 103–109.
Patent Abstracts of Japan, vol. 9, No. 167 (P-372)(1890) 12 Jul. 1985.
Translation of Japanese Patent Application 61-181,947.

*Primary Examiner*—Vincent P. McGraw

[57] ABSTRACT

A method and apparatus for in-process transient spectroscopic analysis of a molten metal, wherein a probe containing a pulsed high-power laser producing a pulsed laser beam having a substantially triangular pulse waveshape is immersed in the molten metal and irradiates a representative quantity of the molten metal. The pulsed laser beam vaporizes a portion of the molten metal to produce a plasma plume having an elemental composition representative of the elemental composition of the molten metal. Before the plasma plume reaches thermal equilibrium shortly after termination of the laser pulse, a spectroscopic detector in the probe detects spectral line reversals, as caused by absorption of radiation emitted by the hotter inner portion of the plasma plume to relatively colder outer portions of the plasma plume, during a short first time window. Thereafter, when the afterglow plasma is in thermal equilibrium, a second spectroscopic detector also in the probe performs a second short time duration spectroscopic measurement. A rangefinder measures and controls the distance between the molten metal surface and the pulsed laser.

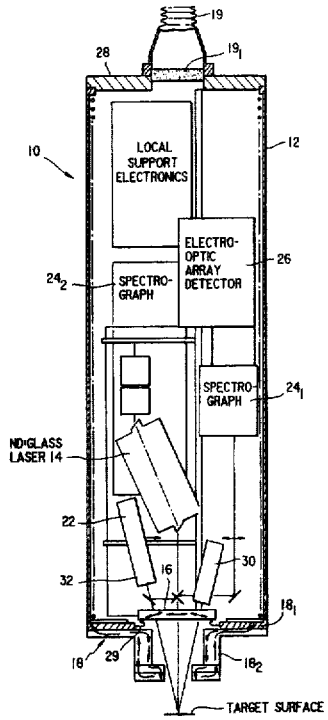

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 11 and 13 are cancelled.

Claims 1–7, 10, 12, 14, 18, 22, 26–29, 32, 34 and 50 are determined to be patentable as amended.

Claims 8, 9, 15–17, 19–21, 23–25, 30, 31, 33, 35–49, 51 and 52, dependent on an amended claim, are determined to be patentable.

New claims 53–56 are added and determined to be patentable.

1. A method for spectroscopic analysis of a molten metal, comprising:
   providing a probe including a casing having an open end adapted to be immersed in the molten metal, laser means disposed in said casing for irradiating the surface of the molten metal adjacent the open end with a laser beam of predetermined energy density and focal spot size, [and] spectroscopic detector means disposed in said casing for detecting spectral components of light emitted from a plasma produced by the laser means *and a rangefinder disposed in said casing for detecting the distance between the molten metal and the laser means*;
   immersing the open end of the casing into the molten metal;
   *detecting the distance between the molten metal and the laser means during immersion of the casing, said detecting being performed without contact with the molten metal;*
   irradiating the molten metal with a laser beam from said laser means to produce a plasma representative of the composition of the molten metal, said irradiating being performed during immersion of the casing open end into the molten metal *when the laser means reaches a predetermined distance from the molten metal as detected by the rangefinder*; [and]
   detecting spectral components of radiation emitted by the plasma by means of the spectroscopic detector means in the casing and producing signals corresponding to the detected spectral components; *and*
   *withdrawing said open end of said casing from the molten metal after irradiating the molten metal and detecting the spectral components.*

2. The method according to claim 1, wherein:
   said irradiating step comprises irradiating said molten metal with a pulsed laser beam; and
   said [detecting] step *of detecting spectral components* comprises detecting spectral line reversals in radiation emitted by said plasma during a predetermined first time window shortly after said pulsed laser beam reaches peak power and prior to said plasma reaching thermal equilibrium.

3. The method according to claim 1, wherein said [detecting] step *of detecting spectral components* comprises:
   detecting spectral components in the radiation emitted by said plasma during a predetermined time window in an afterglow period during which said plasma is in thermal equilibrium.

4. The method according to claim 2, wherein said [detecting] step *of detecting spectral components* comprises:
   detecting spectral components in the radiation emitted by said plasma during a predetermined second time window in an afterglow period during which said plasma is in thermal equilibrium.

5. The method according to claims 1, 2, 3 or 4, wherein said irradiating step comprises:
   irradiating said molten metal with a pulsed laser beam having *a* substantially triangular waveshape with a rise time of 50±20 nsec, a time duration of 50–100 nsec [at the halfwidth] *in full width at half maximum intensity*, a power density greater than $10^9$ W/cm$^2$, and a focal spot size of 1–4 mm$^2$ on the surface of the molten metal.

6. [The] *A* method [according to claim 2,] *for spectroscopic analysis of a molten metal, comprising:*
   *providing a probe including a casing having an open end adapted to be immersed in the molten metal, laser means disposed in said casing for irradiating the surface of the molten metal adjacent the open end with a laser beam of predetermined energy density and focal spot size, and spectroscopic detector means disposed in said casing for detecting spectral components of light emitted from a plasma produced by the laser means;*
   *immersing the open end of the casing into the molten metal;*
   *irradiating the molten metal with a pulsed laser beam from said laser means to produce a plasma representative of the composition of the molten metal, said irradiating being performed during immersion of the casing open end into the molten metal; and*
   *detecting spectral components of radiation emitted by the plasma by means of the spectroscopic detector means in the casing and producing signals corresponding to the detected spectral components, wherein said detecting step comprises detecting spectral line reversals in radiation emitted by said plasma during a predetermined first time window shortly after said pulsed laser beam reaches peak power and prior to said plasma reaching thermal equilibrium, and* wherein said first time window has a time duration of 5–50 nsec and begins 50–500 nsec after the pulsed laser beam reaches peak power.

7. [The] *A* method [according to claims 3,] *for spectroscopic analysis of a molten metal, comprising:*
   *providing a probe including a casing having an open end adapted to be immersed in the molten metal, laser means disposed in said casing for irradiating the surface of the molten metal adjacent the open end with a laser beam of predetermined energy density and focal spot size, and spectroscopic detector means disposed in said casing for detecting spectral components of light emitted from a plasma produced by the laser means;*
   *immersing the open end of the casing into the molten metal;*
   *irradiating the molten metal with a laser beam from said laser means to produce a plasma representative of the*

*composition of the molten metal, said irradiating being performed during immersion of the casing open end into the molten metal; and*

*detecting spectral components of radiation emitted by the plasma by means of the spectroscopic detector means in the casing and producing signals corresponding to the detected spectral components, wherein said detecting step comprises detecting spectral components in the radiation emitted by said plasma during a predetermined time window in an afterglow period during which said plasma is in thermal equilibrium, and wherein said predetermined time window has a time duration of 20–500 nsec and begins between 250 nsec and 5 μsec after initiation of said irradiating step.*

10. The method according to claims 1, 2, 3 or 4, comprising:

said providing step comprising providing [rangefinder means disposed in said casing for detecting the distance between the surface of the molten metal and] a focusing lens [of] *for* said laser means;

introducing an inert gas under pressure into a space between the focusing lens and the surface of the molten metal;

detecting the distance between the surface of the molten metal and the focusing lens using said rangefinding means; and controlling the pressure of the inert gas introduced into said space based on the detected distance between the surface of the molten metal and the focusing lens so that said distance between the surface of the molten metal and the focusing lens is maintained at a predetermined distance.

12. The method according to claim 9, comprising:

said providing step comprising providing [rangefinder means disposed in said casing for detecting the distance between the surface of the molten metal and] a focusing lens [of] *for* said laser means;

introducing an inert gas under pressure into a space between the focusing lens and the surface of the molten metal;

detecting the distance between the surface of the molten metal and the focusing lens using said rangefinding means; and controlling the pressure of the inert gas introduced into said space based on the detected distance between the surface of the molten metal and the focusing lens so that said distance between the surface of the molten metal and the focusing lens is maintained at a predetermined distance.

14. The method according to claim 11, wherein said step of detecting spectral components is performed in relation to a predetermined region of the plasma at a first predetermined distance [of] *from* the surface of the molten metal and a second predetermined distance away from the optical axis of said laser means.

18. The method according to [claims 16] *claim 14*, comprising:

detecting, based on the spectral components detected in said detecting step, peaks in the spectrum represented by the detected spectral componets;

fitting a predetermined function to each detected peak;

forming a synthesized composite spectrum based on the fitted step;

comparing the synthesized composite spectrum with the spectrum represented by the detected spectral components and producing an error signal based on the difference therebetween; and determining whether the error signal is within predetermined limits, and if so, outputting the synthesized composite spectrum as representative of the constituent emission lines of the elements in the molten metal, and if not, modifying the functional fit to each detected peak and iteratively repeating said fitting, comparing and determining steps until said error signal is within said predetermined limits.

22. An apparatus for spectroscopic analysis of a molten metal, comprising:

a probe comprising a casing having an open end adapted to be immersed in the molten metal;

*means for immersing and withdrawing said open end of said casing into the molten metal;*

*laser means disposed in said casing;*

*a rangefinder means disposed in said casing and spaced from contact with the molten metal for detecting the distance between the laser means and the molten metal during immersion of said open end of said casing into the molten metal and indicating when a predetermined distance between said laser means and the molten metal had been detected;* said laser means *being* disposed in said casing for irradiating the surface of the molten metal adjacent to the open end of the casing with a laser beam *during immersion of said open end of said casing and at the predetermined distance from the molten metal as detected by the rangefinder* so as to produce a plasma having a composition representative of the composition of the molten metal; and spectroscopic detecting means disposed in said casing and optically coupled to the plasma for detecting spectral components of radiation emitted by the plasma and producing signals corresponding to the detected spectral components.

26. The apparatus according to claims 22 or 23, wherein said laser means comprises:

a Q-switched laser and a focusing lens which in combination produces at the surface of said molten metal a pulsed laser beam having a substantially triangular waveshape with a rise time of 50±20 nsec, a time duration of 50–100 nsec [at the halfwidth] *in full width at half maximum intensity*, a power density greater than $10^9$ W/cm$^2$, and a focal spot size of 1–4 mm$^2$ on the surface of the molten metal.

27. The apparatus according to claims 23 or 25, wherein said laser means comprises:

a focusing lens which in combination with said Q-switched laser produces at the surface of the molten metal [said molten metal] a pulsed laser beam having *a* substantially triangular waveshape with a rise time of 50±20 nsec, a time duration of 50–100 nsec [at the halfwidth] *in full width at half maximum intensity*, a power density greater than $10^9$ W/cm$^2$, and a focal spot size of 1–3 mm on the surface of the molten metal.

28. [The] *An* apparatus [according to claim 23,] *for spectroscopic analysis of a molten metal, comprising:*

*a probe comprising a casing having an open end adapted to be immersed in the molten metal;*

*laser means disposed in said casing for irradiating the surface of the molten metal adjacent to the open end of the casing with a laser beam so as to produce a plasma having a composition representative of the composition*

*of the molten metal, wherein said laser means comprises a Q-switched pulsed laser which generates a pulsed laser beam; and*

*spectroscopic detecting means disposed in said casing and optically coupled to the plasma for detecting spectral components of radiation emitted by the plasma and producing signals corresponding to the detected spectral components, wherein said spectroscopic detecting means comprises first means for detecting spectral line reversals in radiation emitted by said plasma during a predetermined first time window shortly after said pulsed laser beam reaches peak power and prior to said plasma reaching thermal equilibrium, and wherein said first time window has a time duration of 5–50 nsec and begins 50–500 nsec after the pulsed laser beam reaches peak power.*

29. [The] *An* apparatus [according to claim 24.] *for spectroscopic analysis of a molten metal, comprising:*

*a probe comprising a casing having an open end adapted to be immersed in the molten metal;*

*laser means disposed in said casing for irradiating the surface of the molten metal adjacent to the open end of the casing with a laser beam so as to produce a plasma having a composition representative of the composition of the molten metal; and*

*spectroscopic detecting means disposed in said casing and optically coupled to the plasma for detecting spectral components of radiation emitted by the plasma and producing signals corresponding to the detected spectral components, wherein said spectroscopic detector means comprises means for detecting spectral components in the radiation emitted by said plasma during a predetermined time window in a afterglow period during which said plasma is in thermal equilibrium, and wherein said predetermined time window has a time duration of 20–500 nsec and begins between 250 nsec and 5 μsec after initiation of said irradiating step.*

32. The apparatus according to claims 22 or 24, further comprising:

means *for* introducing an inert gas under pressure into a space between a focusing lens of the laser means and the surface of the molten metal;

*said* rangefinder means [disposed in the casing] for detecting the distance between the surface of the molten metal and the focusing lens; and means for controlling the pressure of the inert gas introduced into said space based on the detected distance between the surface of the molten metal and the focusing lens so that said distance between the surface of the molten metal and the focusing lens is maintained at a predetermined distance.

34. The apparatus according to claim 31, further comprising:

means for introducing an inert gas under pressure into a space between a focusing lens of the laser means and the surface of the molten metal;

*said* rangefinder means [disposed in the casing] for detecting the distance between the surface of the molten metal and the focusing lens; and means for controlling the pressure of the inert gas introduced into said space based on the detected distance between the surface of the molten metal and the focusing lens so that said distance between the surface of the molten metal and the focusing lens is maintained at a predetermined distance.

50. The apparatus according to claim [47] *46*, further comprising:

folded optics means, provided between said radiation separating means and said selection means, including plural mirrors, for reflecting the spectral components separated by said separating means plural times thereby to increase the distance travelled by said spectral components and the spatial separation thereof.

*53. A method for spectroscopic analysis of a molten metal comprising:*

*providing a probe including a casing having an open end adapted to be immersed in the molten metal, laser means disposed in said casing for irradiating the surface of the molten metal adjacent the open end with a laser beam of predetermined energy density and focal spot size, and spectroscopic detector means disposed in said casing for detecting spectral components of light emitted from a plasma produced by the laser means;*

*immersing the open end of the casing into the molten metal;*

*irradiating the molten metal with a laser beam from said laser means to produce a plasma representative of the composition of the molten metal, said irradiating being performed during immersion of the casing open end into the molten metal;*

*detecting spectral components of radiation emitted by the plasma by means of the spectroscopic detector means in the casing and producing signals corresponding to the detected spectral components;*

*detecting, based on the spectral components detected in said detecting step, peaks in the spectrum represented by the detected spectral components;*

*fitting a predetermined function to each detected peak;*

*forming a synthesized composite spectrum based on the fitted step;*

*comparing the synthesized composite spectrum with the spectrum represented by the detected spectral components and producing an error signal based on the difference therebetween; and*

*determining whether the error signal is within predetermined limits, and if so, outputting the synthesized composite spectrum as representative of the constituent emission lines of the elements in the molten metal, and if not, modifying the functional fit to each detected peak and iteratively repeating said fitting, comparing and determining steps until said error signal is within said predetermined limits.*

*54. An apparatus for spectroscopic analysis of a molten metal, comprising:*

*a probe comprising a casing having an open end adapted to be immersed in the molten metal;*

*laser means disposed in said casing for irradiating the surface of the molten metal adjacent to the open end of the casing with a laser beam so as to produce a plasma having a composition representative of the composition of the molten metal; and*

*spectroscopic detecting means disposed in said casing and optically coupled to the plasma for detecting spectral components of radiation emitted by the plasma and producing signals corresponding to the detected spectral components,*

*processing means for processing the signals produced by said spectrograph detecting means by performing the following functions,*

*means for detecting, based on the spectral components detected by said spectroscopic detecting means, peaks* in the spectrum represented by the detected spectral components, means for fitting a predetermined function to each detected peak, means for forming a synthesized composite spectrum based on the fitted function, means for comparing the synthesized composite spectrum with the spectrum represented by the detected spectral components and producing an error signal based on the difference therebetween, and means for determining whether the error signal is within predetermined limits, and if so, outputting the synthesized composite spectrum as representative of the emission lines of the constituent elements in the molten metal, and if not, modifying the functional fit to each detected peak and alternatively repeating said fitting, comparing and determining functions until said error signal is within said predetermined limits.

55. An apparatus for spectroscopic analysis of a molten metal, comprising:

a probe comprising a casing having an open end adapted to be immersed in the molten metal;

laser means disposed in said casing for irradiating the surface of the molten metal adjacent to the open end of the casing with a laser beam so as to produce a plasma having a composition representative of the composition of the molten metal; and spectroscopic detecting means disposed in said casing and optically coupled to the plasma for detecting spectral components of radiation emitted by the plasma and producing signals corresponding to the detected spectral components, wherein said spectroscopic detecting means comprises means for separating radiation emitted from said plasma into plural spectral components;

a gated array of photodetecting pixel elements optically coupled to said radiation separating means to detect the presence of predetermined spectral components; and selection means, including plural segmented mirrors, for selectively reflecting selected of said spatially separated spectral components to selected of said pixel-elements.

56. A method for spectroscopic analysis of a molten metal, comprising:

providing a probe including a casing having an open end adapted to be immersed in the molten metal, laser means disposed in said casing for irradiating the surface of the molten metal adjacent the open end with a laser beam of predetermined energy density and focal spot size, and spectroscopic detector means disposed in said casing for detecting spectral components of light emitted from a plasma produced by the laser means;

immersing the open end of the casing into the molten metal;

irradiating the molten metal with a pulsed laser beam from said laser means to produce a plasma representative of the composition of the molten metal, said laser beam having a substantially triangular waveshape with a rise time of 50±20 nsec, a time duration of 50–100 nsec in full width at half maximum intensity, a power density greater than $10^9$ W/cm$^2$, and a focal spot size of 1–4 mm$^2$ on the surface of the molten metal, said irradiating being performed during immersion of the casing open end into the molten metal; and detecting spectral components of radiation emitted by the plasma by means of the spectroscopic detector means in the casing and producing signals corresponding to the detected spectral components.

\* \* \* \* \*